(12) United States Patent
Allegrini et al.

(10) Patent No.: US 7,692,027 B2
(45) Date of Patent: Apr. 6, 2010

(54) PROCESS FOR THE PREPARATION OF TELMISARTAN

(75) Inventors: Pietro Allegrini, San Donato Milanese (IT); Marcello Rasparini, Pavia (IT); Gabriele Razzetti, Sesto S. Giovanni (IT); Alberto Bologna, Vidigulfo (IT); Giuseppe Barreca, Montevecchia (IT)

(73) Assignee: Dipharma S.p.A., Mereto Di Tomba (IT)

( * ) Notice: Subject to any disclaimer, the term of this patent is extended or adjusted under 35 U.S.C. 154(b) by 752 days.

(21) Appl. No.: 11/415,429

(22) Filed: May 2, 2006

(65) Prior Publication Data

US 2006/0264644 A1    Nov. 23, 2006

(30) Foreign Application Priority Data

May 3, 2005    (IT) .......................... MI2005A0801

(51) Int. Cl.
*C07D 403/04*    (2006.01)
(52) U.S. Cl. .................................... 548/305.4
(58) Field of Classification Search ............... 548/305.4
See application file for complete search history.

(56) References Cited

U.S. PATENT DOCUMENTS

2005/0020654 A1 * 1/2005 Pershadsingh et al. ...... 514/394

FOREIGN PATENT DOCUMENTS

EP    0 502 314 A1    9/1992

OTHER PUBLICATIONS

Tao et al., "A Practical Preparation of 2-Carboxyphenylboronic Acid and its Application for the Preparation of Biaryl-2-carboxylic Acids using Suzuki Coupling Reactions", Synthesis 2002, No. 8, 1043-1046.

* cited by examiner

*Primary Examiner*—Laura L. Stockton
(74) *Attorney, Agent, or Firm*—Rothwell, Figg, Ernst & Manbeck, P.C.

(57) ABSTRACT

A process for the preparation of telmisartan (I) and novel intermediates useful for its synthesis.

(I)

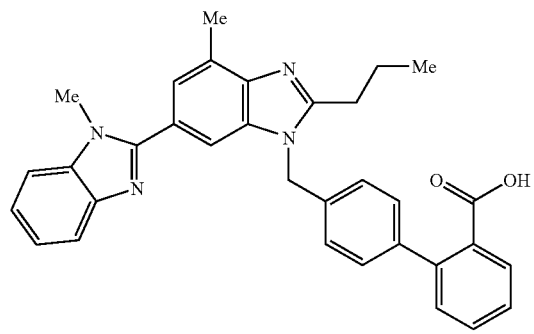

12 Claims, No Drawings

PROCESS FOR THE PREPARATION OF TELMISARTAN

FIELD OF THE INVENTION

The present invention relates to a process for the preparation of telmisartan and novel intermediates for the synthesis thereof.

BACKGROUND OF THE INVENTION

Telmisartan, 4'-[(1,7'-dimethyl-2'-propyl[2,5'-bis-1H-benzimidazol]-3'-yl)methyl][1,1'-biphenyl]-2-carboxylic acid is a known ACE inhibitor useful in therapy as antihypertensive agent. Its preparation is disclosed in EP 502314 and comprises the alkylation of 4-methyl-6-(1-methyl-benzimidazol-2-yl)-2-propylbenzimidazole (A) with t-butyl 4'-(bromomethyl)biphenyl-2-carboxylate (B)

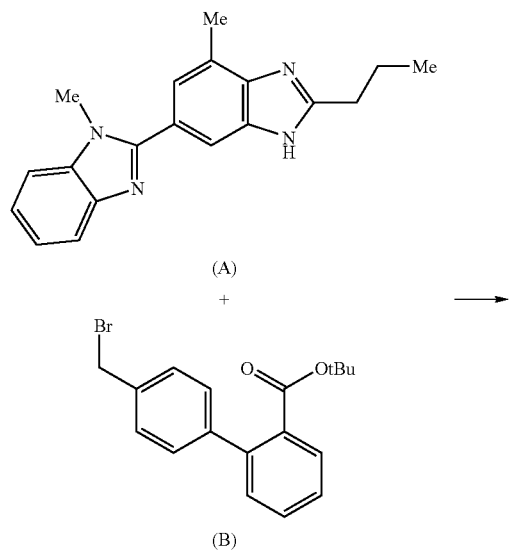

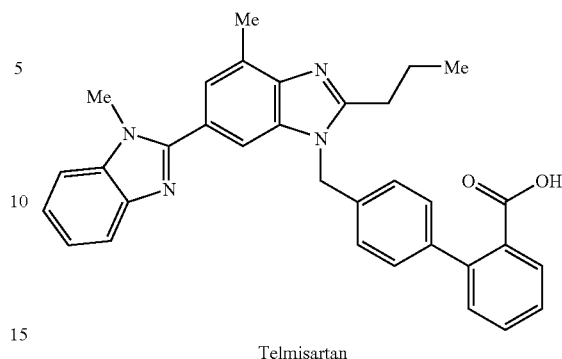

Telmisartan

However, compound (B) is not commercially available and its synthesis requires a n umber of steps, among them the protection of the carboxylic function which is finally removed by hydrolysis. There is therefore the need for an alternative synthesis for the industrial preparation of telmisartan, which makes use of commercially available or easy to prepare intermediates and which, if possible, avoids the additional steps of protection and deprotection of the carboxylic function.

DETAILED DISCLOSURE OF THE INVENTION

The present invention provides a process for the preparation of a compound of formula (I) or a salt thereof.

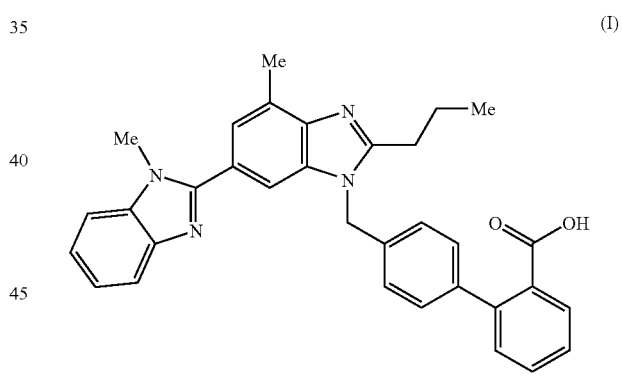

comprising the reaction of a compound of formula (II) or a salt thereof.

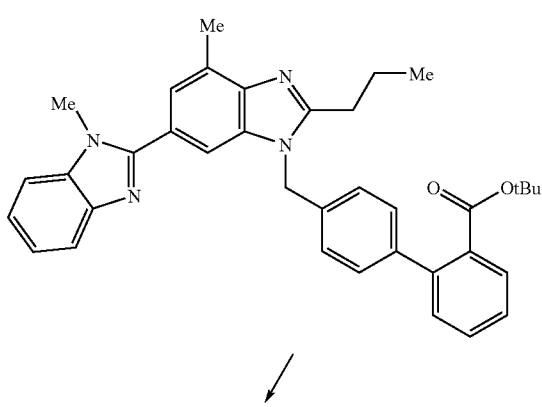

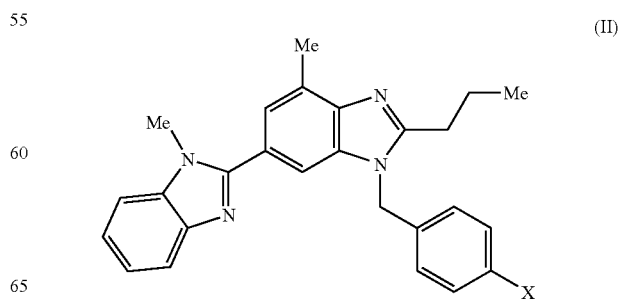

with a synthon of formula (III) or a salt thereof

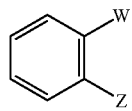

in the presence of a catalyst, an organic ligand and, if necessary, a basic agent, wherein the W is a COOH group, or a W' group which can be transformed into a COOH group;

one of X and Z is a leaving group, while the other one is a group selected from

—B(OR$_1$OR$_2$) wherein R$_1$ and R$_2$ are independently hydrogen, C$_1$-C$_8$ alkyl, aryl, aryl-C$_1$-C$_8$ alkyl or R$_1$ and R$_2$, taken together, form a —(CH$_2$)$_m$—V—(CH$_1$)$_n$ group, wherein m and n, which can be the same or different, are 0 or 1, and V is NR$_3$ or C(R$_3$)$_2$, wherein each R$_3$ is independently hydrogen, C$_1$-C$_8$ alkyl, aryl or aryl-C$_1$-C$_8$ alkyl; a lithium or copper atom or a halogenated metal; and, if necessary, the conversion of the W' group to a —COOH group and/or, if desired, the conversion of a compound of formula (I) to a salt thereof and/or if desired, the conversion of a salt of a compound of formula (I) to its unsalified form.

A salt of a compound of formula (I) or (II) is for example a salt with a pharmaceutically acceptable organic or inorganic base or acid. In particular the sodium, potassium, magnesium or calcium salt or the hydrochloride, hydrobromide, tosylate and camphorsulfate salt. The hydrochloride, hydrobromide, tosylate and camphorsulfate salts of a compound of formula (I) and (II) are novel and are a further object of the invention. A salt of a compound of formula (III) is for example a salt with a base, in particular the sodium, potassium, magnesium or calcium salt.

A W' group is for example a group which can be transformed into a COOH group by hydrolysis or oxidation, typically an ester group, in particular a COOR$_4$ group, wherein R$_4$ is C$_1$-C$_8$ alkyl, aryl or aryl-C$_1$-C$_8$ alkyl; cyano; a CONR$_3$R$_3$ amide or an oxazolidine

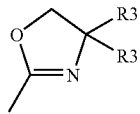

wherein the R$_3$ groups, which may be the same or different, are as defined above; an alcohol group, for example CH$_2$OH, or an aldehyde group, for example CHO.

A C$_1$-C$_8$ alkyl group, which can be straight or branched, is preferably C$_1$-C$_4$ alkyl, in particular methyl, ethyl, propyl, isopropyl, butyl, sec-butyl or ter-butyl.

An aryl group is for example phenyl or naphthyl, preferably phenyl.

A leaving group is typically a halogen atom, for example chlorine, bromine or iodine, in particular bromine; or a hydroxy group activated by esterification, for example with an alkylsulfonyl group, typically methanesulfonyloxy, toluenesulfonyloxy, fluorosulfonyloxy, trifluoromethanesulfonyloxy or nonafluorobutanesulfonyloxy.

A halogenated metal is for example a zinc, magnesium, nickel, copper or boron halide, preferably —ZnCl, —MgCl, —NiCl, —CuCl, —BCl$_2$, —ZnBr, —MgBr, —CuBr, and —BBr$_2$, more preferably ZnCl.

A catalyst is typically a Pd, Pt or Ni salt, such as chloride, bromide, iodide, acetate, acetylacetonate, carbonate, hydroxide, preferably palladium (II) acetate.

An organic ligand is typically a phosphine, such as tricyclohexyl phosphine, triphenylphosphine, tris-(3-hydroxypropyl)-phosphine, tributylphosphine, dppb (1,4-bis(diphenylphosphino)butane), dppf (diphenylphosphinoferrocene), preferably triphenylphosphine.

A basic agent can be an organic base, such as a straight or branched tertiary amine, or an inorganic base, such as potassium or sodium carbonate, cesium carbonate, sodium acetate, sodium hydroxide, potassium phosphate, potassium hydrogen phosphate, preferably potassium carbonate.

The reaction can be carried out in the presence of an organic solvent, typically an aromatic hydrocarbon, for example toluene, xylene; or an ether, for example tetrahydrofuran or dioxane; or an ester, for example ethyl acetate or butyl acetate; or in a dipolar aprotic solvent such as dimethylformamide, dimethylacetamide, dimethylsulfoxide or N-methylpyrrolidone, optionally in admixture with one another or with water.

The reaction can be carried out at a temperature ranging from about 0° C. to the reflux temperature of the reaction mixture, preferably from 30° C. to the reflux temperature, more preferably at the reflux temperature of the mixture.

According to a particularly preferred embodiment of the invention, in a compound of formula (II) X is a leaving group, in particular a bromine atom; in a compound of formula (III) Z is a —B(OR$_1$OR$_2$) group wherein R$_1$ and R$_2$ are as defined above, and in particular R$_1$ and R$_2$ are both hydrogen; and the reaction is carried out in a tetrahydrofuran—water mixture. In a compound of formula (III) W is preferably a COOH group; in this case the direct reaction product is telmisartan. A compound of formula (III) in which W is a W' group can be converted to a compound of formula (III) in which W is —COOH according to known methods. Likewise, the conversion of a compound of formula (I) into a respective salt or the conversion of a salt of a compound of formula (I) to the unsalified form can be accomplished according to known methods.

The synthons of formula (III) are commercially available and can be prepared with known methods. For example, when W is a COOH group and Z is a —B(OR$_1$OR$_2$) group as defined above, the compound can be prepared according to B. Tao et al.: Synthesis (2002), 8, pgg. 1043-1046.

The compounds of formula (II) are novel and are a further object of the invention. The compounds of formula (II) wherein X is a leaving group, typically a halogen atom, in particular bromine, are preferred. These compounds can be obtained by known methods, for example a compound of formula (II) in which X is a leaving group can be prepared by reaction of a compound of formula (IV)

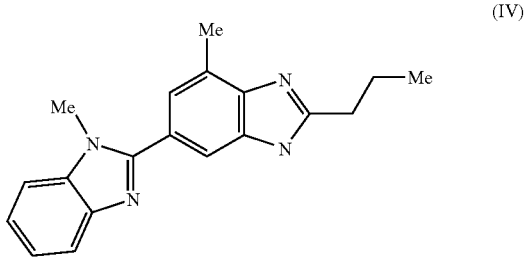

with a compound of formula (V)×

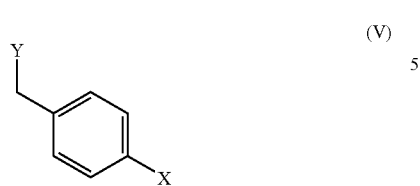

wherein X is a leaving group as defined above and Y is a leaving group, which can be the same as X or different, in the presence of a basic agent.

A basic agent can be an organic or inorganic base, as defined above, preferably potassium carbonate.

The reaction can be carried out in the presence of an organic solvent, typically an aromatic hydrocarbon, for example toluene or xylene; or an ether, for example tetrahydrofuran or dioxane; or an ester, for example ethyl acetate or butyl acetate; or a chlorinated solvent, for example dichloromethane, or an alkanol, for example methanol, ethanol or isopropanol, or a dipolar aprotic solvent, for example dimethylformamide, dimethylacetamide, N-methyl pyrrolidone, dimethylsulfoxide, preferably dimethylacetamide.

The reaction can be carried out at a temperature ranging from about 0° C. to the reflux temperature of the reaction mixture, preferably from 20 to 30° C.

A compound of formula (II) in which X is a —B(OR$_1$OR$_2$) group, a lithium or copper atom or a halogenated metal, can be prepared starting from a compound of formula (II) in which X is a leaving group, as defined above, according to known methods.

In particular, a compound of formula (II) in which X is a halogenated metal, for example a —ZnCl group, can be prepared by reaction of a compound of formula (II) in which X is a leaving group with magnesium, and subsequent exchange of the resulting Grignard compound with zinc chloride.

The compounds of formula (IV) and (V) are known and commercially available.

The following examples illustrate the invention.

EXAMPLE 1

1-(4-Bromobenzyl)-5-(1'-methylbenzimidazol-2'-yl)-4-methyl-2-propyl benzimidazole (II)

2-(5'-Methyl-2-propyl-1H-benzimidazol-6-yl)-1-methyl benzimidazole (2.80 g, 9.2 mmol), dimethylacetamide (14 ml), potassium carbonate (1.27 g, 9.2 mmol) and 4-bromobenzyl bromide (2.30 g, 9.2 mmol) are loaded into a round-bottom flask equipped with mechanical stirrer and thermometer. After stirring at room temperature for 8 hours, the mixture is poured into a 2:1 toluene-water (150 ml) and stirred for 15 minutes at room temperature.

After two washings with water, the aqueous phase is separated and the organic phase is filtered through paper, then evaporated to a residue, which is triturated with 15 ml of hexane, to obtain 3 g of product.

$^1$H NMR (300 MHz, CDCl$_3$): δ (7.76-7.79 (m, 1H), 7.38-7.41 (m, 4H), 7.33-7.35 (m, 1H), 7.26-7.29 (m, 2H), 5.32 (s, 2H), 3.77 (s, 3H), 2.85 (t, J=8.0 Hz, 2H), 2.75 (s, 3H), 1.85 (sext., J=7.5 Hz, 2H), 1.01 (t, J=7.5 Hz, 3H)

EXAMPLE 2

4'-[[4-Methyl-6-(1-methyl-2-benzimidazolyl)-2-propyl-1-benzimidazolyl]methyl]-2-biphenylcarboxylic acid (telmisartan)

2-Carboxyphenyl boronic acid sodium salt (1.17 g, 5.0 mmol) dissolved in 1.5 ml of water, 1-(4-bromobenzyl)-5-(1'-methylbenzimidazol-2'-yl)-4-methyl-2-propyl benzimidazole (1.55 g, 3.3 mmol), tetrahydrofuran (10 ml), potassium carbonate (690 mg, 5.0 mmol), triphenylphosphine (130 mg, 0.50 mmol) and palladium acetate (38 mg, 0.17 mmol) are loaded into a round-bottom flask equipped with magnetic stirrer and condenser, under nitrogen atmosphere. Residual air is removed with nitrogen and the mixture is heated at 60° C. for 18 hours.

After this time the mixture is cooled, added with water (20 ml) and tetrahydrofuran is evaporated off. The residue is taken up with ethyl acetate (10 ml) and acidified with acetic acid to pH=5. The product is filtered and washed with water, to obtain 1.2 g of crude telmisartan, which is purified by dissolution in concentrated ammonia (1 ml), addition of acetone and reprecipitation with acetic acid.

$^1$H NMR (300 MHz, DMSO-d$_6$): δ (7.65-7.70 (m, 3H), 7.40-7.56 (m, 4H), 7.15-7.32 (m, 7H), 5.60 (s, 2H), 3.80 (s, 3H), 2.91 (m, 2H), 2.61 (s, 3H), 1.80 (m, 2H), 0.98 (m, 2H).

$^{13}$C NMR (300 MHz, DMSO-d$_6$): δ (169.50. 156.19, 154.01, 142.70. 142.35, 140.48, 140.16, 136.60. 135.90. 134.70. 132.29, 130.80. 130.32, 129.08, 128.68, 128.21, 127.28, 126.37, 123.14, 122.06, 121.80. 118.65, 110.37, 109.28, 46.12, 31.74, 28.80. 20.71, 16.43, 13.81

EXAMPLE 3

Ethyl 4'-[[4-methyl-6-(1-methyl-2-benzimidazolyl)-2-propyl-1-benzimidazolyl]methyl]-2-biphenylcarboxylate (telmisartan ethyl ester)

1-(4-Bromobenzyl)-5-(1'-methylbenzimidazol-2'-yl)-4-methyl-2-propyl benzimidazole (5.0 g, 10.6 mmol) and tetrahydrofuran (40 ml) are loaded into a round-bottom flask equipped with magnetic stirrer and condenser and under nitrogen atmosphere, then cooled to −78° C. with an acetone/CO$_2$ bath. 2.5 M Butyl lithium in hexane (4.8 ml, 12 mmol) is dropwise added followed by a solution of zinc chloride (2.5 g, 18.4 mmol) in THF (15 ml) after one hour. The temperature is allowed to raise up to 25° C. in 18 hours, then ethyl 2-bromobenzoate (2.45 g, 10.7 mmol), palladium acetate (24 mg, 0.11 mmol) and triphenylphosphine (83 mg, 0.31 mmol) are added.

Residual air is removed with nitrogen and the mixture is heated at 55° C. for 18 hours. The reaction is stopped by addition of 25 ml of a saturated ammonium chloride solution, THF is evaporated off and the product is extracted with ethyl acetate, then crystallized from ethyl acetate/hexane to obtain 4 g of product.

EXAMPLE 4

4'-[[4-Methyl-6-(1-methyl-2-benzimidazolyl)-2-propyl-1-benzimidazolyl]methyl]-2-biphenylcarboxylic acid (telmisartan)

(4'-Methyl-2'-propyl-1H-benzimidazol-6-yl)-1-methyl benzimidazole (3.0 g, 9.8 mmol), 4-(4,4,5,5-tetramethyl[1,3,2]dioxaborolan-2-yl)benzyl methanesulfonate (3.12 g, 10 mmol), tetrahydrofuran (15 ml) and potassium carbonate (1.38 g, 10 mmol) are loaded into a round-bottom flask equipped with magnetic stirrer, condenser and under nitrogen atmosphere. The mixture is stirred at room temperature for 8 hours, then 10% hydrochloric acid is added to pH=2.

THF is evaporated off, which causes precipitation of boronic acid. After recrystallization from ethyl acetate, 4.2 g of product are obtained.

The boronic acid (3.5 g, 8.0 mmol), ethyl 2-bromoacetate (1.83 g, 8.0 mmol), sodium hydroxide (1.28 g, 32 mmol), water (5 ml), tetrahydrofuran (20 ml), triphenylphosphine (315 mg, 1.2 mmol) and palladium acetate (90 mg, 0.4 mmol) are loaded into a round-bottom flask equipped with magnetic stirrer and condenser. All the residual air is removed with nitrogen and then the mixture is heated at 60° C. for 18 hours, thereafter is cooled, added with water (30 ml) and tetrahydrofuran is evaporated off. Ethyl acetate is added (30 ml) and the mixture is acidified with acetic acid to pH=5. The product is filtered and washed with water, to obtain 2.8 g of crude telmisartan, which is purified by dissolution in concentrated ammonia (2 ml), addition of acetone and reprecipitation with acetic acid.

EXAMPLE 5

4'-[[4-Methyl-6-(1-methyl-2-benzimidazolyl)-2-propyl-1-benzimidazolyl]methyl]-2-biphenylcarboxylic acid sodium salt (telmisartan sodium salt)

10 g of telmisartan are suspended in 40 ml of THF in a round-bottom flask equipped with magnetic stirrer, condenser and under nitrogen atmosphere. The solution is added with 1.5 ml of 50% aq NaOH and the mixture is heated under reflux, then evaporated to a residue. 10.4 g of telmisartan sodium salt are obtained.

EXAMPLE 6

4'-[[4-Methyl-6-(1-methyl-2-benzimidazolyl)-2-propyl-1-benzimidazolyl]methyl]-2-biphenylcarboxylic acid hydrochloride (telmisartan hydrochloride)

10 g of telmisartan are suspended in 70 ml of methanol in a round-bottom flask equipped with magnetic stirrer, condenser and under nitrogen atmosphere. The solution is added with 2.0 ml of a 37% HCl aqueous solution and the mixture is heated under reflux, then cooled to room temperature. The resulting precipitate is filtered and dried under vacuum at 55° C. to obtain 7.5 g of telmisartan hydrochloride.

The invention claimed is:

1. A process for the preparation of a compound of formula (I) or a salt thereof

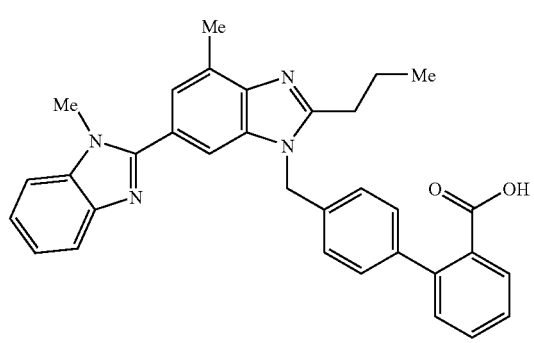

comprising the reaction of a compound of formula (II) or a salt thereof

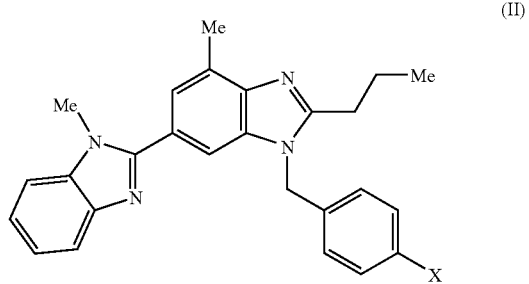

with a synthon of formula (III) or a salt thereof

in the presence of a catalyst, an organic ligand and, if necessary, a basic agent;

wherein

W is a COOH group, or a W' group which can be transformed into a COOH group;

one of X and Z is a leaving group, while the other one is a group of formula —B(OR$_1$OR$_2$) wherein R$_1$ and R$_2$ are independently hydrogen, C$_1$-C$_8$ alkyl, aryl, aryl-C$_1$-C$_8$ alkyl or R$_1$ and R$_2$, taken together, form a —(CH$_2$)$_m$—V—(CH$_2$)$_n$ group, wherein m and n, which can be the same or different, are 0 or 1, and V is NR$_3$ or C(R$_3$)$_2$ wherein each R$_3$ is independently hydrogen, C$_1$-C$_8$ alkyl, aryl or aryl- C$_1$-C$_8$ alkyl; a lithium or copper atom or a halogenated metal; and, if necessary, the conversion of the W' group to a —COOH group and/or, if desired, the conversion of a compound of formula (I) to a salt and/or, if desired, the conversion of a salt of a compound of formula (I) to its unsalified form.

2. A process according to claim 1, wherein the catalyst is a Pd, Pt or Ni salt.

3. A process according to claim 2, wherein the catalyst is palladium (II) acetate.

4. A process according to claim 1, wherein the organic ligand is a phosphine.

5. A process according to claim 4, wherein the organic ligand is tricyclohexyl phosphine, triphenylphosphine, tris- (3-hydroxypropyl)-phosphine, tributylphosphine, 1,4-bis(diphenylphosphino)butane or diphenylphosphinoferrocene.

6. A process according to claim 5, wherein the organic ligand is triphenylphosphine.

7. A process according to claim 1, wherein the basic agent is an organic or an inorganic base.

8. A process according to claim 7, wherein the basic agent is potassium carbonate.

9. A process according to claim 1, wherein in a compound of formula (II) X is a leaving group, in a compound of formula (III) Z is a $—B(OR_1\ OR_2)$ group wherein $R_1$ and $R_2$ are as defined in claim 1, and the reaction is carried out in a tetrahydrofuran — water mixture.

10. A process according to claim 9, wherein the leaving group is a bromine atom.

11. A process according to claim 9, wherein $R_1$ and $R_2$ are hydrogen.

12. A process according to claim 9, wherein in a compound of formula (III) W is a COOH group.

* * * * *